(12) United States Patent
Wang et al.

(10) Patent No.: US 10,125,110 B2
(45) Date of Patent: Nov. 13, 2018

(54) METHOD FOR PREPARING 2,5-DISUBSTITUTED FURAN COMPOUND

(71) Applicant: Ningbo Institute of Materials Technology & Engineering, Chinese Academy of Sciences, Ningbo (CN)

(72) Inventors: Jinggang Wang, Ningbo (CN); Xiaoqing Liu, Ningbo (CN); Jin Zhu, Ningbo (CN); Haining Na, Ningbo (CN)

(73) Assignee: Ningbo Institute of Materials Technology & Engineering, Chinese Academy of Sciences, Ningbo, Zhejiang (CN)

( * ) Notice: Subject to any disclaimer, the term of this patent is extended or adjusted under 35 U.S.C. 154(b) by 0 days.

(21) Appl. No.: 15/535,075

(22) PCT Filed: Dec. 17, 2014

(86) PCT No.: PCT/CN2014/094066
§ 371 (c)(1),
(2) Date: Jun. 12, 2017

(87) PCT Pub. No.: WO2016/090658
PCT Pub. Date: Jun. 16, 2016

(65) Prior Publication Data
US 2017/0320844 A1 Nov. 9, 2017

(30) Foreign Application Priority Data

Dec. 11, 2014 (CN) .......................... 2014 1 0763313
Dec. 11, 2014 (CN) .......................... 2014 1 0763428
Dec. 11, 2014 (CN) .......................... 2014 1 0765238

(51) Int. Cl.
*C07D 307/46* (2006.01)
*C07D 307/36* (2006.01)

(52) U.S. Cl.
CPC ......... *C07D 307/46* (2013.01); *C07D 307/36* (2013.01)

(58) Field of Classification Search
CPC ........................... C07D 307/46; C07D 307/36
See application file for complete search history.

(56) References Cited

FOREIGN PATENT DOCUMENTS

CN 102120735 A 7/2011

OTHER PUBLICATIONS

Shen, Yongmiao et al., "Synthesis of 5-Methyl-2-propionylfuran with Sulfonic Acidic Ionic Liquid as Catalyst", Applied Chemical Industry, Jan. 28, 2011, pp. 82, 83 and 87, vol. 40, No. 1.
Liu, Xudong et al., "Synthesis of 2,5-Diethyltetrahydrofuran with Mint Smell", Flavour Fragrance Cosmetics, Oct. 30, 2012, pp. 14 to 16 and 24, No. 5.
Triantafyllakis, M. et al., "Singlet Oxygen-mediated Synthesis of Bis-spiroketals Found in Azaspiracids", Organic Letters, May 28, 2014, pp. 3150 to 3153, vol. 16, No. 11.
Kitamura, C. et al., "Synthesis and Crystallochromy of 1,4,7,10-Tetraalkyltetracenes: Tuning of Solid-State Optical Properties of Tetracenes by Alkyl Side-Chain Length", Chemistry—A European Journal, Nov. 20, 2009, pp. 890 to 898, vol. 16.
Snegaroff, K. et al., "Deprotonative Metalation of Functionalized Aromatics Using Mixed Lithium—Cadmium, Lithium—Indium, and Lithium—Zinc Species", Chemistry—A European Journal, Aug. 17, 2009, pp. 10280 to 10290, vol. 15.
Rickborn, Bruce, "The Retro-Diels-Alder Reaction Part I. C-C Dienophiles", Organic Reactions, 1998, pp. 1 to 8, vol. 52.
Uchiyama, M. et al., "Highly enantioselective reduction of symmetrical diacetylaromatics with baker's yeast", Tetrahedron: Asymmetry, 1997, pp. 3467 to 3474, vol. 8, No. 20.
Yahata et al., "Methodology for in Situ Protection of Aldehydes and Ketones Using Trimethylsilyl Trifluoromethanesulfonate and Phosphines: Selective Alkylation and Reduction of Ketones, Esters, Amides, and Nitriles", Chem. Pharm. Bull., Sep. 21, 2013, pp. 1298 to 1307, vol. 61, No. 12, The Pharmaceutical Society of Japan.
Yoon et al., "Supporting Information for Phenyl-, pyrrole-, and furan-containing diametrically strapped calix[4]pyrroles. An experimental and theoretical study of hydrogen bonding effects in chloride anion recognition", Angewandte Chemie, Jun. 16, 2008.
Wang et al., "Tandem reactions of Friedel-Crafts/aldehyde cyclotrimerization catalyzed by an organotungsten Lewis acid", Tetrahedron Letters, 2002, pp. 1051 to 1055, vol. 43, Elsevier Science Ltd.
Khusnutdinov et al., "Synthesis of methyl furan-2-carboxylate and dimethyl furan-2,5-dicarboxylate by copper-catalyzed reactions of furans with CCl4 and MeOH", Russian Chemical Bulletin, International Edition, Jan. 2013, pp. 93 to 97, vol. 62, No. 1, Springer Science+Business Media, Inc.

*Primary Examiner* — Timothy R Rozof
(74) *Attorney, Agent, or Firm* — Edwin A. Sisson, Attorney at Law, LLC; Jeffrey J. Banyas

(57) ABSTRACT

Disclosed is a method for preparing a 2,5-disubstituted furan compound. The 2,5-disubstituted furan compound is prepared in a simple, convenient and highly efficient way by reacting 2,3-dicarboxylic anhydride-7-oxabicyclo[2.2.1]hept-5-ene and/or furan with an acylating reagent and/or an alkylating reagent. The preparation method is simple and efficient, has a short process and less by-products, and the 2,5-disubstituted furan compound prepared by using the method has a high purity, and can satisfy the requirements for being used as a raw material for engineering plastics, such as high-performance polyesters, epoxy resins, polyamides, polyurethanes and the like, and as a chemical raw material and a pharmaceutical intermediate raw material.

14 Claims, 2 Drawing Sheets

METHOD FOR PREPARING 2,5-DISUBSTITUTED FURAN COMPOUND

PRIORITIES AND CROSS REFERENCES

This patent application claims priority from International Application No. PCT/CN2014/094066 filed on 17 Dec. 2014, Chinese Application No. 201410763313.2 filed on 11 Dec. 2014, Chinese Application No. 2014107665238.3 filed on 11 Dec. 2014, and Chinese Application No. 201410763428.1 filed on 11 Jun. 2014, the teachings of each of which are incorporated herein by reference in their entirety.

TECHNICAL FIELD

The present application relates to a method for preparing a 2,5-disubstituted furan compound, which belongs to the technical fields of the preparation of polymer monomers for such as high-performance polyesters, epoxy resins, polyamides and polyurethanes and the like, as well as the preparation of chemical engineering and pharmaceutical intermediates.

TECHNICAL BACKGROUND

At present, monomers such as alcohols, acids, and esters with a rigid ring structure are single raw materials in the synthesis of high-performance engineering plastics such as polyesters, epoxy resins, polyamides, polyurethanes, and the like. Furan is an important aromatic monomer. However, as a bifunctional reactive group is not present in the structure of furan, furan cannot be directly used for the preparation of high-performance polymers, and the application of furan in the fields of medicine and chemical engineering is also limited.

Since 2,5-disubstituted furan compounds contain a rigid furan ring and a structure of para-diacyl, they can be oxidized or reduced to furan diacids or furan diols, which can be directly used in the preparation of high-performance engineering plastics such as polyesters, epoxy resins, polyamides, polyurethane, and the like. The polymers prepared using furan diacids and furan diols have excellent mechanical properties in terms of strength, modulus, creep resistance, and the like, and simultaneously have higher glass transition temperature and heat distortion temperature. In addition, 2,5-disubstituted furan compounds per se can also be used as chemical raw materials and pharmaceutical intermediates. At present, there are few reports on the synthesis of 2,5-disubstituted furan compounds. Chief among these reports is that a 2,5-diacylfuran compound was synthesized by Uchiyama M et al. with 2-acetylfuran as a raw material [Tetrahedron: Asymmetry, 1997, 8 (20): 3467-3474]. However, this method has the disadvantages of complicated synthesis route, low total yield and high cost, and it is difficult to realize large-scale industrial application.

SUMMARY OF THE INVENTION

According to an aspect of the present application, there is provided a method for preparing a 2,5-disubstituted furan compound. A 2,5-disubstituted furan compound is prepared in a simple, convenient and highly efficient way by reacting 2,3-dicarboxylic anhydride-7-oxabicyclo[2.2.1]hept-5-ene and/or furan with an acylating reagent or an alkylating reagent. The preparation method is simple and efficient, and has a short process and fewer by-products. The 2,5-disubstituted furan compound prepared by using the method has a high purity, and can satisfy the requirements for being used as a raw material for engineering plastics, such as high-performance polyesters, epoxy resins, polyamides, polyurethanes and the like, and as a chemical raw material and a pharmaceutical intermediate raw material.

The method for preparing a 2,5-disubstituted furan compound, wherein the 2,5-disubstituted furan compound is prepared by reacting 2,3-dicarboxylic anhydride-7-oxabicyclo[2.2.1]hept-5-ene and/or furan with an acylating reagent or an alkylating reagent.

Preferably, 2,3-dicarboxylic anhydride-7-oxabicyclo[2.2.1]hept-5-ene is prepared by Dies-Alder reaction (abbreviated as D-A reaction) of furan with maleic anhydride. The molar ratio of furan to maleic anhydride (furan:maleic anhydride) is from 1:0.1 to 1:2. The D-A reaction is performed at a temperature ranging from −10° C. to 100° C. for 0.1 to 48 hours. The chemical structure of 2,3-dicarboxylic anhydride-7-oxabicyclo[2.2.1]hept-5-ene is shown as Formula VI:

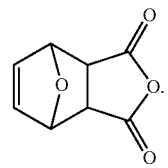

Formula VI

Preferably, the acylating reagent is an anhydride and/or an acyl halide.

Preferably, the alkylating reagent is at least one selected from the group consisting of halogenated alkanes.

The acylation reaction of 2,3-dicarboxylic anhydride-7-oxabicyclo[2.2.1]hept-5-ene with an anhydride is shown as Formula VII-1, and the acylation reaction of furan with an anhydride is shown as Formula VII-2:

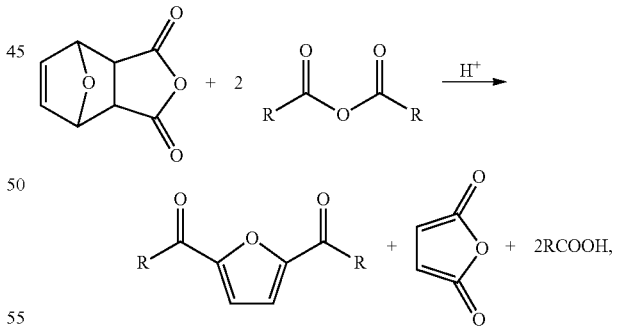

Formula VII-1

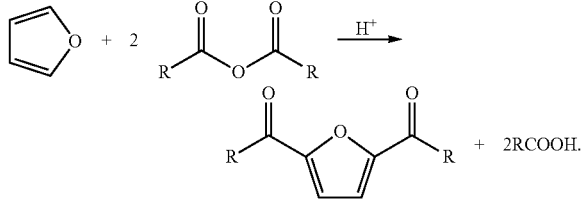

Formula VII-2

The acylation reaction of 2,3-dicarboxylic anhydride-7-oxabicyclo[2.2.1]hept-5-ene with an acyl halide is shown as Formula VIII-1, and the acylation reaction of furan with an acyl halide is shown as Formula VIII-2:

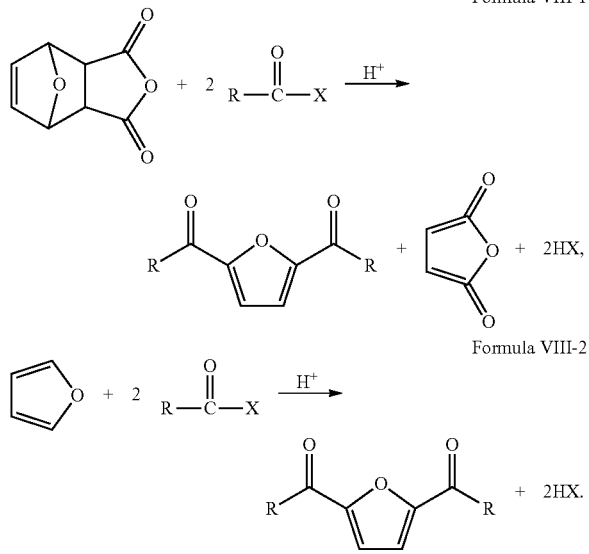

The alkylation reaction of 2,3-dicarboxylic anhydride-7-oxabicyclo[2.2.1]hept-5-ene with a halogenated alkane is shown as Formula IX-1, and the alkylation reaction of furan with a halogenated alkane is shown as Formula IX-2:

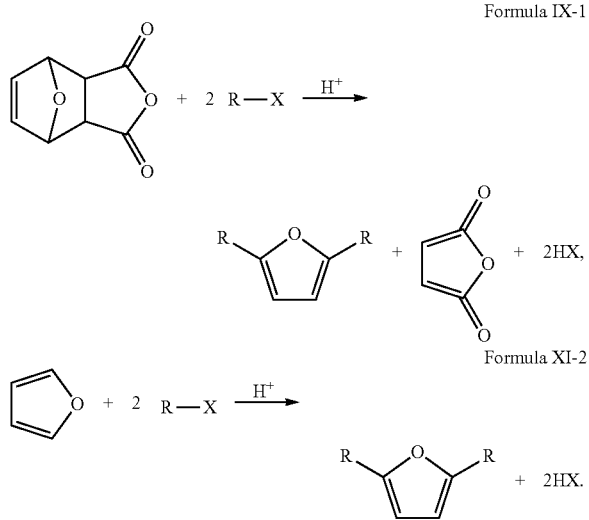

Preferably, the anhydride is at least one selected from the group consisting of compounds with the chemical structure formula represented by Formula I:

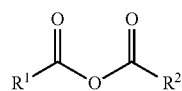

Formula I wherein, $R^1$ is hydrogen or an alkyl group with carbon atoms from 1 to 20; or $R^1$ is a group which is selected from groups with carbon atoms from 1 to 20 and comprising at least one group selected from halogen, aryl, heteroaryl, carbonyl, aliphatic group, nitrile group;

$R^2$ is hydrogen or an alkyl group with carbon atoms from 1 to 20; or $R^2$ is a group which is selected from groups with carbon atoms from 1 to 20 carbon atoms and comprising at least one group selected from halogen, aryl, heteroaryl, carbonyl, aliphatic group, nitrile group;

Preferably, the anhydride is at least one selected from the group consisting of formic anhydride, acetic anhydride, propionic anhydride, butyric anhydride, pentanoic anhydride, caproic anhydride, heptanoic anhydride, octanoic anhydride, nonanoic anhydride, capric anhydride, undecanoic anhydride, dodecanoic anhydride, tridecanoic anhydride, tetradecanoic anhydride, pentadecanoic anhydride, hexadecanoic anhydride, heptadecanoic anhydride, octadecanoic anhydride, chloroacetic anhydride, benzoic anhydride, trifluoroacetic anhydride, trichloroacetic anhydride, tribromoacetic anhydride, triiodoacetic anhydride, heptafluorobutyric anhydride, and pentafluoropropionic anhydride.

Preferably, the acyl halide is at least one selected from the compounds with the chemical structure formula represented by Formula II:

Formula II wherein, $R^3$ is hydrogen or an alkyl group with carbon atoms from 1 to 20; or $R^3$ is selected from groups with carbon atoms from 1 to 20 and comprising at least one group selected from the list consisting of halogen, aryl, heteroaryl, carbonyl, aliphatic group, nitrile group; and X is selected from fluorine, chlorine, bromine, iodine.

Preferably, the $R^3(CO)$— group without X in Formula II is at least one selected from the group consisting of 2-fluoroacetyl, 2-chloroacetyl, 2-bromoacetyl, 2-iodoacetyl, 3-fluoropropionyl, 3-chloropropionyl, 3-bromopropionyl, 3-iodopropionyl, dichloro acetyl, 2-bromopropionyl, furoyl, oxalyl, oxalyl monoethyl ester, phenylacetyl, isobutyryl, benzoyl, methyl oxalyl, hydrocinnamoyl, and diphenylacetyl.

Preferably, the acyl halide is at least one selected from the group consisting of acetyl chloride, acetyl bromide, acetyl iodide, propionyl chloride, butyryl chloride, 2-fluoroacetyl chloride, 2-chloroacetyl chloride, 2-bromoacetyl chloride, 2-iodoacetyl chloride, 3-fluoropropionyl chloride, 3-chloropropionyl chloride, 3-bromopropionyl chloride, 3-iodopropionyl chloride, dichloroacetyl chloride, 2-bromopropionyl chloride, furoyl chloride, oxalyl chloride, monoethyl oxalyl chloride, phenylacetyl chloride, isobutyryl chloride, benzoyl chloride, methyl oxalyl chloride, hydrocinnamyl chloride, and diphenylacetyl chloride.

Preferably, the halogenated alkane is at least one selected from the compounds with the chemical structure formula represented by Formula III:

Formula III wherein, $R^4$ is an alkyl group with carbon atoms from 1 to 20; and X is selected from fluorine, chlorine, bromine, iodine. Preferably, $R^4$ is selected from the group consisting of methyl, ethyl, propyl, butyl, isopropyl, isobutyl, tert-butyl, and cyclohexyl.

Preferably, the 2,5-disubstituted furan compound is at least one selected from the compounds with the chemical structure formula represented by Formula IV or Formula V:

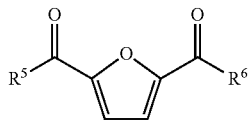

Formula IV wherein, $R^5$ is hydrogen or an alkyl group with carbon atoms from 1 to 20; or $R^5$ is selected from groups with carbon atoms from 1 to 20 and comprising at least one group selected from the list consisting of halogen, aryl, heteroaryl, carbonyl, aliphatic group, nitrile group;

$R^6$ is hydrogen or an alkyl group with carbon atoms from 1 to 20; or $R^6$ is selected from groups with carbon atoms from 1 to 20 and comprising at least one group selected from the list consisting of halogen, aryl, heteroaryl, carbonyl, aliphatic group, nitrile group;

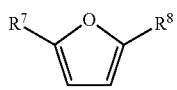

Formula V wherein, $R^7$ is an alkyl group with carbon atoms from 1 to 20; and $R^8$ is an alkyl group with carbon atoms from 1 to 20.

The alkyl group is a group obtained by removing a hydrogen atom from an alkane. The alkane is at least one selected from the group consisting of linear alkanes, branched alkanes, and naphthenes.

The aryl or heteroaryl group is a group obtained by removing a hydrogen atom on the aromatic ring from an aromatic compound. When heteroatoms such as N, O, S, or the like are not present in the aromatic ring, the obtained group is an aryl group; while when heteroatoms such as N, O, S, or the like are present in the aromatic ring, the obtained group is a heteroaryl group. The aromatic compound, which forms an aryl or heteroaryl group, may or may not have substituents on its aromatic ring. Typically, the examples of the substituents are alkyl, carboxyl, hydroxyl, halogeno-group, and the like.

A group comprising at least one group selected from the list consisting of halogen, aryl, heteroaryl, carbonyl, aliphatic group, and nitrile group, is a group which comprises at least one selected from the list consisting of halogen, aryl, heteroaryl, carbonyl, aliphatic group, and nitrile group. For instance, a chloracetyl group is a group comprising both a chloride atom and a carbonyl group.

Preferably, $R^1$ and $R^2$ of Formula I, $R^3$ of Formula II, and $R^5$ and $R^6$ of Formula IV are each independently selected from the group consisting of H, —$CH_3$, —$CH_2CH_3$, —$CHCH_3CH_3$, —$CF_3$, —$CCl_3$, —$CH_2F$, —$CI_3$, —$CH_2Cl$, —$CH_2Br$, —$CHCl_2$, —$CH_2CH_2F$, —$CH_2CH_2Cl$, —$CH_2CH_2Br$, —$CH_2CH_2I$, —$CH_3CHBr$, —$CF_3CF_2$, —$CF_3CF_2CF_2$, furyl, —COCl, $CH_3CH_2OCO$—, $C_6H_5CH_2$—, —$C_6H_5$, $CH_3OCO$—, $C_6H_5CH_2CH_2$—, and $(C_6H_5)_2CH$—.

Preferably, each of $R^1$ and $R^2$ of Formula I, $R^3$ of Formula II, and $R^5$ and $R^6$ of Formula IV is hydrogen atom, or $R^1$ and $R^2$ of Formula I, $R^3$ of Formula II, and $R^5$ and $R^6$ of Formula IV are the same.

Preferably, $R^4$ of Formula III, and $R^7$ and $R^8$ of Formula V are each independently selected from the group consisting of methyl, ethyl, propyl, butyl, isopropyl, isobutyl, tert-butyl, and cyclohexyl.

Preferably, $R^4$ of Formula III, and $R^7$ and $R^8$ of Formula V are the same alkyl.

Preferably, the 2,5-disubstituted furan compound is at least one selected from the group consisting of 2,5-diacetyl-furan, 2,5-dihaloacetylfuran, 2,5-dimethylfuran, and 2,5-diethylfuran.

Preferably, the reaction of 2,3-dicarboxylic anhydride-7-oxabicyclo[2.2.1]hept-5-ene and/or furan with the acylating reagent is performed at a temperature ranging from 10° C. to 200° C. and for a time ranging 0.1 to 48 hours.

Further preferably, the upper limit of the temperature of the acylation reaction is selected from the group consisting of 200° C., 180° C., 160° C., 120° C., and 100° C., and the lower limit is selected from the group consisting of 30° C., 40° C., 50° C., 60° C., 70° C., and 80° C.

Preferably, the reaction of 2,3-dicarboxylic anhydride-7-oxabicyclo[2.2.1]hept-5-ene and/or furan with the alkylating reagent is performed at a temperature ranging from 20° C. to 160° C. and for a time ranging 1 to 24 hours.

Further preferably, the upper limit of the temperature of the alkylation reaction is selected from the group consisting of 160° C., 140° C., 120° C., and 100° C., and the lower limit is selected from the group consisting of 40° C., 50° C., 60° C., 70° C., and 80° C.

Preferably, in the reaction of 2,3-dicarboxylic anhydride-7-oxabicyclo[2.2.1]hept-5-ene and/or furan with the acylating reagent, the molar ratio of the acylating reagent to 2,3-dicarboxylic anhydride-7-oxabicyclo[2.2.1]hept-5-ene and/or furan is that:

moles of the acylating reagent: (moles of 2,3-dicarboxylic anhydride-7-oxabicyclo[2.2.1]hept-5-ene+moles of furan) is in a range from 1:1 to 20:1;

wherein, in the reaction of 2,3-dicarboxylic anhydride-7-oxabicyclo[2.2.1]hept-5-ene and/or furan with the alkylating reagent, the molar ratio of the alkylating reagent to 2,3-dicarboxylic anhydride-7-oxabicyclo[2.2.1]hept-5-ene and/or furan is that:

moles of the alkylating reagent (moles of 2,3-dicarboxylic anhydride-7-oxabicyclo[2.2.1]hept-5-ene+moles of furan) is in a range from 1:1 to 20:1.

Preferably, an acid catalyst is used in the reaction of 2,3-dicarboxylic anhydride-7-oxabicyclo[2.2.1]hept-5-ene and/or furan with the acylating reagent; and the molar ratio of the acid catalyst to the acylating reagent is that moles of the acid catalyst:moles of the acylating reagent is in a range from 0.002%:1 to 20%:1.

Preferably, an acid catalyst is used in the reaction of 2,3-dicarboxylic anhydride-7-oxabicyclo[2.2.1]hept-5-ene and/or furan with the alkylating reagent; and the molar ratio of the acid catalyst to the alkylating reagent is that moles of the acid catalyst:moles of the alkylating reagent is in a range from 0.002%:1 to 20%:1.

The acid catalyst is at least one selected from sulfuric acid, nitric acid, phosphoric acid, hydrochloric acid, methanesulfonic acid, aluminum chloride, zinc chloride, tin chloride, boron trifluoride ethyl ether complex.

The beneficial effects of the present application include, but are not limited to the following effects: The technical solution according to the present application establishes a simple and efficient technique for chemical conversion with short process flow and fewer by-products, in which the furan is used as a raw material effectively and a 2,5-disubstituted furan compound is prepared from furan in two steps, with a total yield of 70% to 90%.

The technical solution according to the present application provides an important raw material for the synthesis of high-performance polyesters, epoxy resins and polyurethanes, can fully assist in raising the manufacturing level of high performance engineering plastics, and can promote getting rid of the high dependency on oil resources in the bio-based polymer material industry.

DETAILED DESCRIPTION OF THE EMBODIMENT

Hereinafter, the present invention will be described in further detail in combination with the Examples. It will be appreciated that these Examples are merely illustrative of the present application and are not intended to limit the scope of the present application.

In the Examples, $^1$H-NMR spectra were measured by using 400 AVANCE Type III Spectrometer from Bruker (400 MHz, CDCl$_3$).

Elemental analysis was performed by using the Perkin-Elmer 2400 II CHN mode and O mode.

The products were analyzed by using 7890B-5977A Liquid Chromatography-Mass Spectrometer (Agilent).

The yield of 2,3-dicarboxylic anhydride-7-oxabicyclo [2.2.1]hept-5-ene was calculated by using the following equation:

Yield %=(mass of 2,3-dicarboxylic anhydride-7-oxabicyclo[2.2.1]hept-5-ene×100)/[(moles of furan×68) or moles of maleic anhydride x 98)].

The yield of a 2,5-disubstituted furan compound was calculated by using the following equation:

Yield %=(mass of 2,5-disubstituted furan compound×100)/(moles of 2,3-dicarboxylic anhydride-7-oxabicyclo[2.2.1]hept-5-ene×166+moles of furan×68).

Example 1

Figure 1:
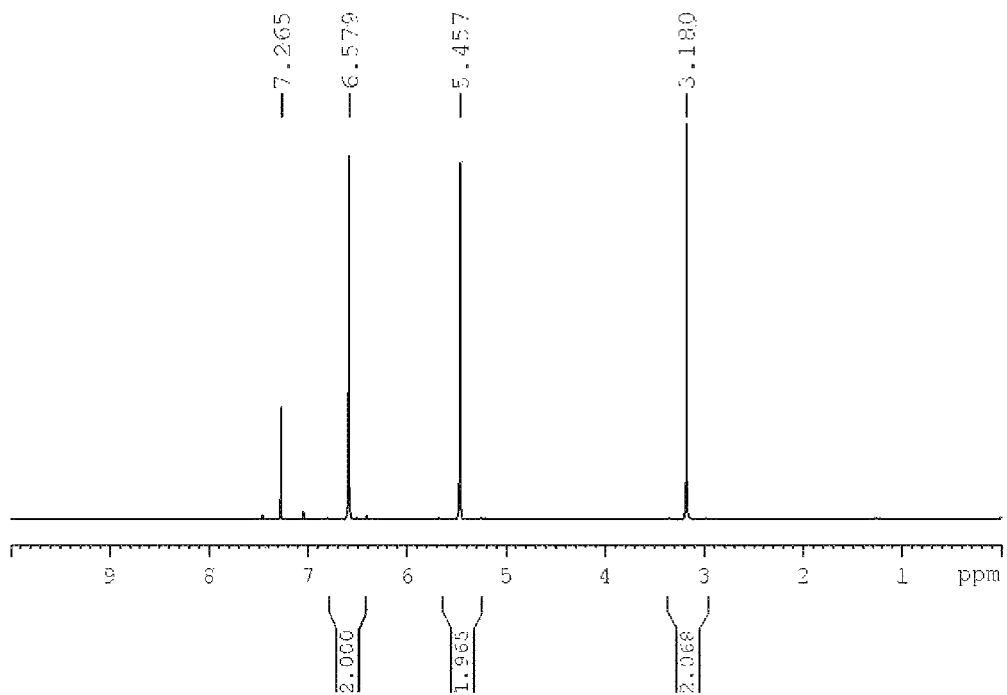
FIG. 1 shows an $^1$H-NMR spectrum of the 2,3-dicarboxylic anhydride-7-oxabicyclo[2.2.1] hept-5-ene obtained in Example 1.

In a 500 ml reactor, 68.0 g of furan, 78.5 g of maleic anhydride, and 100 ml of toluene were added, and reacted at 50° C. for 10 hours. The resultant was cooled, crystallized, and dried to give white crystals of 2,3-dicarboxylic anhydride-7-oxabicyclo[2.2.1]hept-5-ene, with a yield of 92%. It was showed from the $^1$H-NMR (400 MHz, CDCl$_3$) spectrum that there were three peaks of CH, 2H of the ring, δ(3.18, 5.46, 6.58), respectively, as shown in FIG. 1.

Figure 2:
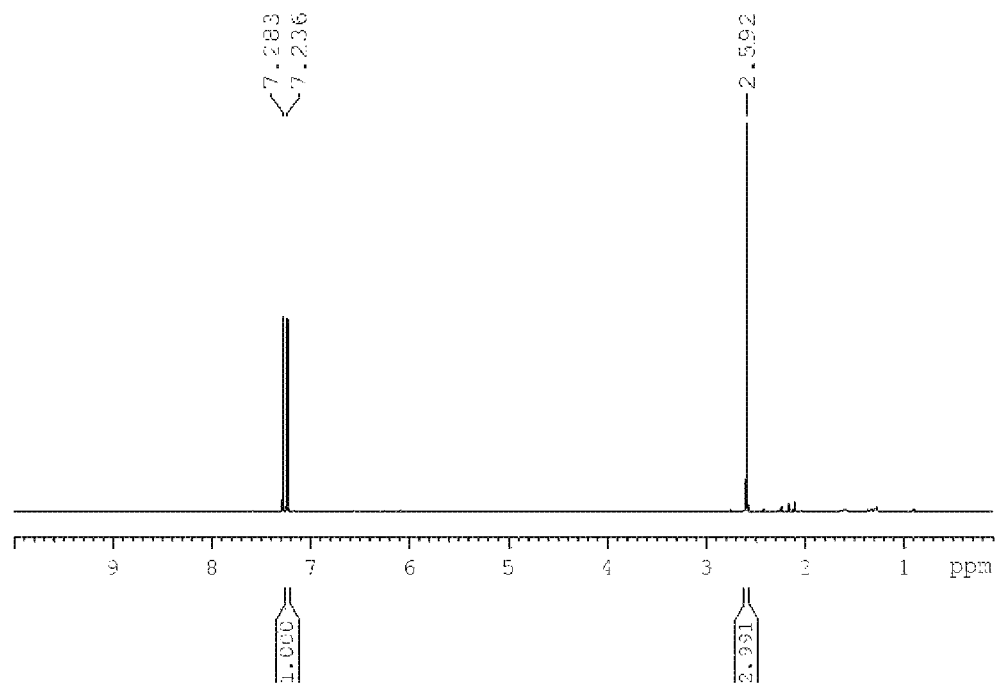
FIG. 2 shows an $^1$H-NMR spectrum of 2,5-diacetylfuran obtained in Example 1.

16.6 g of 2,3-dicarboxylic anhydride-7-oxabicyclo[2.2.1] hept-5-ene was added into a 100 ml reactor. 20.4 g of acetic anhydride and 0.02 mol of concentrated sulfuric acid were added thereto and reacted at 160° C. for 4 hours. After the reaction was finished, the temperature was reduced to room temperature. The resultant was distilled to remove acetic anhydride under reduced pressure and sublimated to give white crystals of 2,5-diacetylfuran having a melting point ranging from 135° C. to 136° C., and the yield was 86%. The molecular weight of 2,5-diacetylfuran was 152.1, which was measured by liquid chromatography-mass spectrometry (LC-MS). It was showed from the $^1$H-NMR (400 MHz, CDCl$_3$) spectrum that: furan ring: CH, 2H: δ(7.24), CH$_3$, 6H: δ(2.59), as shown in FIG. 2. Elemental analysis for C$_8$H$_8$O$_3$: Calculated: C: 63.15, H: 5.30, O: 31.55. Found: C: 62.8, H: 5.27, O: 31.57.

Example 2

In a 500 ml reactor, 68.0 g of furan, 19.6 g of maleic anhydride, and 20 ml of dichloromethane were added, and reacted at 100° C. for 1 hour. The resultant was cooled, crystallized, and dried to give white crystals of 2,3-dicarboxylic anhydride-7-oxabicyclo[2.2.1]hept-5-ene, with a yield of 90%. It was showed from the $^1$H-NMR (400 MHz, CDCl$_3$) spectrum that there were three peaks of CH, 2H of the ring, δ(3.18, 5.46, 6.58), respectively.

16.6 g of 2,3-dicarboxylic anhydride-7-oxabicyclo[2.2.1] hept-5-ene was added into a 100 ml reactor. 45.0 g of formic anhydride and 0.025 mol of concentrated nitric acid were added thereto and reacted at 180° C. for 2 hours. After the reaction was finished, the temperature was reduced to room temperature. The resultant was distilled to remove acetic anhydride under reduced pressure and sublimated to give white crystals of 2,5-diformoxylfuran, with a yield of 92%. The molecular weight of 2,5-diformoxylfuran was 124.1, which was measured by liquid chromatography-mass spectrometry (LC-MS). It was showed from the $^1$H-NMR (400 MHz, CDCl$_3$) spectrum that: furan ring: CH, 2H, δ(7.54); CHO, 2H, δ(9.60). Elemental analysis for C$_6$H$_4$O$_3$: Calculated: C: 58.07, H: 3.25, O: 38.68. Found: C: 57.9, H: 3.26, O: 38.10.

Example 3

In a 500 ml reactor, 68.0 g of furan, 9.8 g of maleic anhydride, and 10 ml of trichloromethane were added, and reacted at 70° C. for 2 hours. The resultant was cooled, crystallized, and dried to give white crystals of 2,3-dicarboxylic anhydride-7-oxabicyclo[2.2.1]hept-5-ene, with a yield of 96%. It was showed from the $^1$H-NMR (400 MHz, CDCl$_3$) spectrum that there were three peaks of CH, 2H of the ring, δ(3.18, 5.46, 6.58), respectively.

8.3 g of 2,3-dicarboxylic anhydride-7-oxabicyclo[2.2.1] hept-5-ene was added into a 100 ml reactor. 73.1 g of propionic anhydride and 0.005 mol of concentrated hydrochloric acid were added thereto and reacted at 120° C. for 8 hours. After the reaction was finished, the temperature was reduced to room temperature. The resultant was distilled to remove propionic anhydride under reduced pressure and sublimated to give white crystals of 2,5-dipropionylfuran, with a yield of 88%. The molecular weight of 2,5-dipropionylfuran was 180.1, which was measured by liquid chromatography-mass spectrometry (LC-MS). It was showed from the $^1$H-NMR (400 MHz, CDCl$_3$) spectrum that: furan ring: CH, 2H, δ(7.24); CH$_2$, 4H, δ(2.78); CH$_3$, 6H, δ(1.22). Elemental analysis for C$_{10}$H$_{12}$O$_3$: Calculated: C: 66.65, H: 6.71, O: 26.64. Found: C: 66.4, H: 6.51, O: 27.1.

Example 4

In a 500 ml reactor, 68.0 g of furan, and 24.5 g of maleic anhydride were added, and reacted at 30° C. for 6 hours. The resultant was crystallized and dried to give white crystals of 2,3-dicarboxylic anhydride-7-oxabicyclo[2.2.1]hept-5-ene, with a yield of 92%. It was showed from the $^1$H-NMR (400 MHz, CDCl$_3$) spectrum that there were three peaks of CH, 2H of the aromatic ring, δ(3.18, 5.46, 6.58), respectively.

16.6 g of 2,3-dicarboxylic anhydride-7-oxabicyclo[2.2.1]hept-5-ene was added into a 100 ml reactor. 8.7 g of butyric anhydride and 0.005 mol of methanesulfonic acid were added thereto and reacted at 100° C. for 12 hours. After the reaction was finished, the temperature was reduced to room temperature. The resultant was distilled to remove butyric anhydride under reduced pressure and sublimated to give white crystals of 2,5-dibutyrylfuran, with a yield of 81%. The molecular weight of 2,5-dibutyrylfuran was 208.3, which was measured by liquid chromatography-mass spectrometry (LC-MS). It was showed from the $^1$H-NMR (400 MHz, CDCl$_3$) spectrum that: furan ring: CH, 2H, δ(7.24); CH$_2$, 4H, δ(2.74); CH$_2$, 4H, δ(1.52); CH$_3$, 6H, δ(0.96). Elemental analysis for C$_{12}$H$_{16}$O$_3$: Calculated: C: 69.21, H: 7.74, O: 23.05. Found: C: 69.10, H: 7.47, O: 23.22.

Example 5

In a 500 ml reactor, 68.0 g of furan, 117.7 g of maleic anhydride, and 200 ml of acetone were added, and reacted at 10° C. for 16 hours. The resultant was crystallized and dried to give white crystals of 2,3-dicarboxylic anhydride-7-oxabicyclo[2.2.1]hept-5-ene, with a yield of 88%. It was showed from the $^1$H-NMR (400 MHz, CDCl$_3$) spectrum that there were three peaks of CH, 2H of the aromatic ring, δ(3.18, 5.46, 6.58), respectively.

16.6 g of 2,3-dicarboxylic anhydride-7-oxabicyclo[2.2.1]hept-5-ene monomer was added into a 100 ml reactor. 20.2 g of pentanoic anhydride and 0.01 mol of benzene methyl sulfonic acid were added thereto and reacted at 10° C. for 48 hours. After the reaction was finished, the temperature was increased to room temperature. The resultant was distilled to remove pentanoic anhydride under reduced pressure and sublimated to give white crystals of 2,5-divalerylfuran, with a yield of 94%. The molecular weight of 2,5-divalerylfuran was 236.3, which was measured by liquid chromatography-mass spectrometry (LC-MS). It was showed from the $^1$H-NMR (400 MHz, CDCl$_3$) spectrum that: furan ring: CH, 2H, δ(7.24); CH$_2$, 4H, δ(2.74); CH$_2$, 4H, δ(1.48); CH$_2$, 4H, δ(1.33); CH$_3$, 6H, δ(0.96). Elemental analysis for C$_{14}$H$_{20}$O$_3$: Calculated: C: 71.16, H: 8.53, O: 20.31. Found: C: 71.12, H: 7.95, O: 21.08.

Example 6

In a 1000 ml reactor, 68.0 g of furan, 137.2 g of maleic anhydride, and 400 ml of methanol were added, and reacted at 0° C. for 24 hours. The resultant was crystallized and dried to give white crystals of 2,3-dicarboxylic anhydride-7-oxabicyclo[2.2.1]hept-5-ene, with a yield of 90%. It was showed from the $^1$H-NMR (400 MHz, CDCl$_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene was added into a 250 ml reactor. 92.1 g of caproic anhydride and 0.00005 mol of concentrated phosphoric acid were added thereto and reacted at 0° C. for 36 hours. After the reaction was finished, the temperature was increased to room temperature. The resultant was distilled to remove caproic anhydride under reduced pressure and sublimated to give white crystals of 2,5-dicaproylfuran, with a yield of 88%. The molecular weight of 2,5-dicaproylfuran was 264.4, which was measured by liquid chromatography-mass spectrometry (LC-MS). It was showed from the $^1$H-NMR (400 MHz, CDCl$_3$) spectrum that: furan ring: CH, 2H, δ(7.24); CH$_2$, 4H, δ(2.74); CH$_2$, 4H, δ(1.48); CH$_2$, 4H, δ(1.33); CH$_2$, 4H, δ(1.29); CH$_3$, 6H, δ(0.96). Elemental analysis for C$_{16}$H$_{24}$O$_3$: Calculated: C: 72.69, H: 9.15, O: 18.16. Found: C: 72.61, H: 9.10, O: 18.04.

Example 7

In a 2000 ml reactor, 68.0 g of furan, 176.4 g of maleic anhydride, and 1000 ml of ethanol were added, and reacted at −5° C. for 48 hours. The resultant was crystallized and dried to give white crystals of 2,3-dicarboxylic anhydride-7-oxabicyclo[2.2.1]hept-5-ene, with a yield of 92%. It was showed from the $^1$H-NMR (400 MHz, CDCl$_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene was added into a 500 ml reactor. 205.4 g of capric anhydride and 0.012 mol of AlCl$_3$ were added thereto and reacted at 200° C. for 0.1 hour. After the reaction was finished, the temperature was reduced to room temperature. The resultant was distilled to remove capric anhydride under reduced pressure and sublimated to give white crystals of 2,5-dicaprylfuran, with a yield of 84%. The molecular weight of 2,5-dicaprylfuran was 376.6, which was measured by liquid chromatography-mass spectrometry (LC-MS). It was showed from the $^1$H-NMR (400 MHz, CDCl$_3$) spectrum that: furan ring: CH, 2H, δ(7.24); CH$_2$, 4H, δ(2.74); CH$_2$, 4H, δ(1.48); CH$_2$, 20H, δ(1.31); CH$_2$, 4H, δ(1.36); CH$_3$, 6H, δ(0.96). Elemental analysis for C$_{24}$H$_{40}$O$_3$: Calculated: C: 76.55, H: 10.71, O: 12.75. Found: C: 76.21, H: 9.97, O: 12.40.

Example 8

In a 250 ml reactor, 68.0 g of furan, 58.8 g of maleic anhydride, and 5 ml of chloroform were added, and reacted at 20° C. for 12 hours. The resultant was crystallized and dried to give white crystals of 2,3-dicarboxylic anhydride-7-oxabicyclo[2.2.1]hept-5-ene, with a yield of 89%. It was showed from the $^1$H-NMR (400 MHz, CDCl$_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene was added into a 250 ml reactor. 40.8 g of hexadecanoic anhydride and 0.005 mol of ZnCl$_2$ were added thereto and reacted at 80° C. for 1 hour. After the reaction was finished, the temperature was reduced to room temperature. The resultant was distilled to remove hexadecanoic anhydride under reduced pressure and sublimated to give white crystals of 2,5-dihexadecanoylfuran, with a yield of 92%. The molecular weight of 2,5-dihexadecanoylfuran was 544.5, which was measured by liquid chromatography-mass spectrometry (LC-MS). It was showed from the $^1$H-NMR (400 MHz, CDCl$_3$) spectrum that: furan ring: CH, 2H, δ(7.24); CH$_2$, 4H, δ(2.74); CH$_2$, 4H, δ(1.48); CH$_2$, 20H, δ(1.31); CH$_2$, 4H, δ(1.36); CH$_3$, 6H, δ(0.96). Elemental analysis for C$_{36}$H$_{64}$O$_3$: Calculated: C: 79.35, H: 11.84, O: 8.81. Found: C: 79.20, H: 11.66, O: 8.74.

Example 9

In a 500 ml reactor, 68.0 g of furan, 78.5 g of maleic anhydride, and 100 ml of toluene were added, and reacted at 50° C. for 10 hours. The resultant was cooled, crystallized, and dried to give white crystals of 2,3-dicarboxylic anhydride-7-oxabicyclo[2.2.1]hept-5-ene, with a yield of 92%. It was showed from the $^1$H-NMR (400 MHz, CDCl$_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene was added into a 100 ml reactor. 15.7 g of acetyl chloride and 0.001 mol of SnCl$_4$ were added thereto and reacted at 100° C. for 6 hours. After the reaction was finished, the temperature was reduced to room temperature. The resultant was distilled to remove acetyl chloride under reduced pressure and sublimated to give white crystals of 2,5-diacetylfuran having a melting point ranging from 135° C. to 136° C., and the yield was 88%. The molecular weight of 2,5-diacetylfuran was 152.1, which was measured by liquid chromatography-mass spectrometry (LC-MS). It was showed from the $^1$H-NMR (400 MHz, CDCl$_3$) spectrum that: furan ring: CH, 2H, δ(7.24); CH$_3$, 6H, δ(2.59). Elemental analysis for C$_8$H$_8$O$_3$: Calculated: C: 63.15, H: 5.30, O: 31.55. Found: C: 62.9, H: 5.33, O: 31.43.

Example 10

In a 500 ml reactor, 68.0 g of furan, 78.5 g of maleic anhydride, and 100 ml of toluene were added, and reacted at 50° C. for 10 hours. The resultant was cooled, crystallized, and dried to give white crystals of 2,3-dicarboxylic anhydride-7-oxabicyclo[2.2.1]hept-5-ene, with a yield of 92%. It was showed from the $^1$H-NMR (400 MHz, CDCl$_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene was added into a 100 ml reactor. 24.6 g of acetyl bromide and 0.001 mol of boron trifluoride ethyl ether complex were added thereto and reacted at 100° C. for 6 hours. After the reaction was finished, the temperature was reduced to room temperature. The resultant was distilled to remove acetyl bromide under reduced pressure and sublimated to give white crystals of 2,5-diacetylfuran having a melting point ranging from 135° C. to 136° C., and the yield was 87%. The molecular weight of 2,5-diacetylfuran was 152.1, which was measured by liquid chromatography-mass spectrometry (LC-MS). It was showed from the $^1$H-NMR (400 MHz, CDCl$_3$) spectrum that: furan ring: CH, 2H, δ(7.24); CH$_3$, 6H, δ(2.59). Elemental analysis for C$_8$H$_8$O$_3$: Calculated: C: 63.15, H: 5.30, O: 31.55. Found: C: 63.1, H: 5.29, O: 31.40.

Example 11

In a 500 ml reactor, 68.0 g of furan, 78.5 g of maleic anhydride, and 100 ml of toluene were added, and reacted at 50° C. for 10 hours. The resultant was cooled, crystallized, and dried to give white crystals of 2,3-dicarboxylic anhydride-7-oxabicyclo[2.2.1]hept-5-ene, with a yield of 92%. It was showed from the $^1$H-NMR (400 MHz, CDCl$_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene was added into a 100 ml reactor. 34.0 g of acetyl iodine and 0.001 mol of concentrated sulfuric acid were added thereto and reacted at 100° C. for 6 hours. After the reaction was finished, the temperature was reduced to room temperature. The resultant was distilled to remove acetyl iodine under reduced pressure and sublimated to give white crystals of 2,5-diacetylfuran having a melting point ranging from 135° C. to 136° C., and the yield was 90%. The molecular weight of 2,5-diacetylfuran was 152.1, which was measured by liquid chromatography-mass spectrometry (LC-MS). It was showed from the $^1$H-NMR (400 MHz, CDCl$_3$) spectrum that: furan ring: CH, 2H, δ(7.24); CH$_3$, 6H, δ(2.59). Elemental analysis for C$_8$H$_8$O$_3$: Calculated: C: 63.15, H: 5.30, O: 31.55. Found: C: 63.20, H: 5.33, O: 31.60.

Example 12

In a 500 ml reactor, 68.0 g of furan, 24.5 g of maleic anhydride, and 60 ml of petroleum ether were added, and reacted at 30° C. for 6 hours. The resultant was crystallized and dried to give white crystals of 2,3-dicarboxylic anhydride-7-oxabicyclo[2.2.1]hept-5-ene, with a yield of 90%. It was showed from the $^1$H-NMR (400 MHz, CDCl$_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene was added into a 100 ml reactor. 21.3 g of butyryl chloride and 0.001 mol of concentrated sulfuric acid were added thereto and reacted at 120° C. for 12 hours. After the reaction was finished, the temperature was reduced to room temperature. The resultant was distilled to remove butyryl chloride under reduced pressure and sublimated to give white crystals of 2,5-dibutyrylfuran, with a yield of 92%. The molecular weight of 2,5-dibutyrylfuran was 208.3, which was measured by liquid chromatography-mass spectrometry (LC-MS). It was showed from the $^1$H-NMR (400 MHz, CDCl$_3$) spectrum that: furan ring: CH, 2H, δ(7.24); CH$_2$, 4H, δ(2.74); CH$_2$, 4H, δ(1.52), CH$_3$, 6H; δ(0.96). Elemental analysis for C$_{12}$H$_{16}$O$_3$: Calculated: C: 69.21, H: 7.74, O: 23.05. Found: C: 69.15, H: 7.52, O: 22.94.

Example 13

In a 500 ml reactor, 68.0 g of furan, 19.6 g of maleic anhydride, and 20 ml of dichloromethane were added, and reacted at 100° C. for 1 hour. The resultant was cooled, crystallized, and dried to give white crystals of 2,3-dicarboxylic anhydride-7-oxabicyclo[2.2.1]hept-5-ene monomer, with a yield of 90%. It was showed from the $^1$H-NMR (400 MHz, CDCl$_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene monomer was added into a 250 ml reactor. 102.6 g of chloroacetic anhydride and 0.025 mol of concentrated nitric acid were added thereto and reacted at 200° C. for 0.5 hour. After the reaction was finished, the temperature was reduced to room temperature. The resultant was distilled to remove chloroacetic anhydride under reduced pressure and sublimated to give white crystals of 2,5-dichloroacetylfuran, with a yield of 93%. The molecular weight of 2,5-dichloroacetylfuran was 221.0, which was measured by liquid chromatography-mass spectrometry (LC-MS). It was showed from the $^1$H-NMR (400 MHz, CDCl$_3$) spectrum that: furan ring: CH, 2H, δ(7.24); CH$_2$Cl, 4H, δ(4.83).

Example 14

In a 500 ml reactor, 68.0 g of furan, 9.8 g of maleic anhydride, and 10 ml trichloromethane were added, and reacted at 70° C. for 2 hours. The resultant was cooled, crystallized, and dried to give white crystals of 2,3-dicarboxylic anhydride-7-oxabicyclo[2.2.1]hept-5-ene monomer, with a yield of 96%. It was showed from the $^1$H-NMR (400 MHz, CDCl$_3$) spectrum that there were three peaks of CH, 2H of the ring, δ(3.18, 5.46, 6.58), respectively.

8.3 g of 2,3-dicarboxylic anhydride-7-oxabicyclo[2.2.1]hept-5-ene monomer was added into a 250 ml reactor. 57.8 g of trifluoroacetic anhydride and 0.005 mol of concentrated hydrochloric acid were added thereto and reacted at 160° C. for 6 hours. After the reaction was finished, the temperature was reduced to room temperature. The resultant was distilled to remove trifluoroacetic anhydride under reduced pressure and sublimated to give white crystals of 2,5-di(trifluoroacetyl)furan, with a yield of 88%. The molecular weight of 2,5-di(trifluoroacetyl)furan was 260.1, which was measured by liquid chromatography-mass spectrometry (LC-MS). It was showed from the $^1$H-NMR (400 MHz, $CDCl_3$) spectrum that: furan ring: CH, 2H, δ(8.14).

Example 15

In a 500 ml reactor, 68.0 g of furan, 24.5 g of maleic anhydride, and 60 ml of petroleum ether were added, and reacted at 30° C. for 6 hours. The resultant was crystallized and dried to give white crystals of 2,3-dicarboxylic anhydride-7-oxabicyclo[2.2.1]hept-5-ene monomer, with a yield of 92%. It was showed from the $^1$H-NMR (400 MHz, $CDCl_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene monomer was added into a 100 ml reactor. 15.5 g of heptafluorobutyric anhydride and 0.005 mol of concentrated phosphoric acid were added thereto and reacted at 100° C. for 12 hours. After the reaction was finished, the temperature was reduced to room temperature. The resultant was distilled to remove heptafluorobutyric anhydride under reduced pressure and sublimated to give crystals of 2,5-di(heptafluorobutyryl)furan, with a yield of 83%. The molecular weight of 2,5-di-heptafluorobutyrylfuran was 360.1, which was measured by liquid chromatography-mass spectrometry (LC-MS). It was showed from the $^1$H-NMR (400 MHz, $CDCl_3$) spectrum that: furan ring: CH, 2H, δ(7.34).

Example 16

In a 500 ml reactor, 68.0 g of furan, and 117.7 g of maleic anhydride were added, and reacted at 10° C. for 16 hours. The resultant was crystallized and dried to give white crystals of 2,3-dicarboxylic anhydride-7-oxabicyclo[2.2.1]hept-5-ene monomer, with a yield of 88%. It was showed from the $^1$H-NMR (400 MHz, $CDCl_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene monomer was added into a 100 ml reactor. 7.85 g of acetyl chloride and 0.01 mol of methanesulfonic acid were added thereto and reacted at 10° C. for 40 hours. After the reaction was finished, the temperature was increased to room temperature. The resultant was distilled to remove acetyl chloride under reduced pressure and sublimated to give white crystals of 2,5-diacetylfuran, with a yield of 91%. The molecular weight of 2,5-diacetylfuran was 152.1, which was measured by liquid chromatography-mass spectrometry (LC-MS). It was showed from the $^1$H-NMR (400 MHz, $CDCl_3$) spectrum that: furan ring: CH, 2H, δ(7.24); $CH_3$, 6H, δ(2.59). Elemental analysis for $C_8H_8O_3$: Calculated: C: 63.15, H: 5.30, O: 31.55. Found: C: 62.9, H: 5.33, O: 31.43.

Example 17

In a 1000 ml reactor, 68.0 g of furan, 137.2 g of maleic anhydride, and 400 ml of methanol were added, and reacted at 0° C. for 24 hours. The resultant was crystallized and dried to give white crystals of 2,3-dicarboxylic anhydride-7-oxabicyclo[2.2.1]hept-5-ene monomer, with a yield of 90%. It was showed from the $^1$H-NMR (400 MHz, $CDCl_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene monomer was added into a 250 ml reactor. 90.4 g of chloroacetyl chloride and 0.0005 mol of benzene methyl sulfonic acid were added thereto and reacted at 40° C. for 24 hours. After the reaction was finished, the temperature was reduced to room temperature. The resultant was distilled to remove chloroacetyl chloride under reduced pressure and sublimated to give white crystals of 2,5-dichloroacetylfuran, with a yield of 88%. The molecular weight of 2,5-dichloroacetylfuran was 221.0, which was measured by liquid chromatography-mass spectrometry (LC-MS). It was showed from the $^1$H-NMR (400 MHz, $CDCl_3$) spectrum that: furan ring: CH, 2H, δ(7.24); $CH_2Cl$, 4H, δ(4.83).

Example 18

In a 2000 ml reactor, 68.0 g of furan, 176.4 g of maleic anhydride, and 1000 ml of ethanol were added, and reacted at −5° C. for 48 hours. The resultant was crystallized and dried to give white crystals of 2,3-dicarboxylic anhydride-7-oxabicyclo[2.2.1]hept-5-ene monomer, with a yield of 92%. It was showed from the $^1$H-NMR (400 MHz, $CDCl_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene monomer was added into a 250 ml reactor. 14.7 g of dichloroacetyl chloride and 0.012 mol of $AlCl_3$ were added thereto and reacted at 80° C. for 12 hours. After the reaction was finished, the temperature was reduced to room temperature. The resultant was distilled to remove dichloroacetyl chloride under reduced pressure and sublimated to give crystals of 2,5-di(dichloroacetyl)furan, with a yield of 84%. The molecular weight of 2,5-di(dichloroacetyl)furan was 289.9, which was measured by liquid chromatography-mass spectrometry (LC-MS). It was showed from the $^1$H-NMR (400 MHz, $CDCl_3$) spectrum that: furan ring: CH, 2H, δ(7.24); $CHCl_2$, 2H, δ(6.32).

Example 19

In a 250 ml reactor, 68.0 g of furan, 58.8 g of maleic anhydride, and 5 ml of chloroform were added, and reacted at 20° C. for 12 hours. The resultant was crystallized and dried to give white crystal of 2,3-dicarboxylic anhydride-7-oxabicyclo[2.2.1]hept-5-ene monomer, with a yield of 89%. It was showed from the $^1$H-NMR (400 MHz, $CDCl_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene monomer was added into a 250 ml reactor. 156.6 g of furoyl chloride and 0.005 mol of $ZnCl_2$ were added thereto and reacted at 180° C. for 1 hour. After the reaction was finished, the temperature was reduced to room temperature. The resultant was distilled to remove furoyl chloride under reduced pressure and sublimated to give white crystals of 2,5-difuroylfuran, with a yield of 92%. The molecular weight of 2,5-difuroylfuran was 256.2, which was measured by liquid chromatography-mass spectrometry (LC-MS). It was showed from the $^1$H-NMR (400 MHz, $CDCl_3$) spectrum that: furan ring: CH, 2H, δ(7.54); CH, 2H; δ(7.23); CH, 2H, δ(6.61); CH, 2H, δ(7.72).

Example 20

In a 500 ml reactor, 68.0 g of furan, 78.5 g of maleic anhydride, and 100 ml of toluene were added, and reacted at 50° C. for 10 hours. The resultant was cooled, crystallized, and dried to give white crystals of 2,3-dicarboxylic anhydride-7-oxabicyclo[2.2.1]hept-5-ene monomer, with a yield of 92%. It was showed from the $^1$H-NMR (400 MHz, CDCl$_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene monomer was added into a 500 ml reactor. 204.8 g of oxalyl chloride monoethyl ester and 0.001 mol of SnCl$_4$ were added thereto and reacted at 100° C. for 8 hours. After the reaction was finished, the temperature was reduced to room temperature. The resultant was distilled to remove oxalyl chloride monoethyl ester under reduced pressure and sublimated to give white crystals of 2,5-di(monoethyl ester acetyl) furan, with a yield of 89%. The molecular weight of 2,5-di(monoethyl ester acetyl)furan was 268.2, which was measured by liquid chromatography-mass spectrometry (LC-MS). It was showed from the $^1$H-NMR (400 MHz, CDCl$_3$) spectrum that: furan ring: CH, 2H, δ(7.24); CH$_2$, 4H, δ(4.20); CH$_3$, 6H, δ(1.30).

Example 21

In a 500 ml reactor, 68.0 g of furan, 78.5 g of maleic anhydride, and 100 ml of toluene were added, and reacted at 50° C. for 10 hours. The resultant was cooled, crystallized, and dried to give white crystals of 2,3-dicarboxylic anhydride-7-oxabicyclo[2.2.1]hept-5-ene monomer, with a yield of 92%. It was showed from the $^1$H-NMR (400 MHz, CDCl$_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene monomer was added into a 250 ml reactor. 56.2 g of benzoyl chloride and 0.001 mol of boron trifluoride ethyl ether complex were added thereto and reacted at 140° C. for 4 hours. After the reaction was finished, the temperature was reduced to room temperature. The resultant was distilled to remove benzoyl chloride under reduced pressure and sublimated to give white crystals of 2,5-dibenzoylfuran, with a yield of 92%. The molecular weight of 2,5-dibenzoylfuran was 276.3, which was measured by liquid chromatography-mass spectrometry (LC-MS). It was showed from the $^1$H-NMR (400 MHz, CDCl$_3$) spectrum that: furan ring: CH, 2H, δ(7.24); benzene ring, 4H, δ(7.81); benzene ring, 4H, δ(7.45); benzene ring, 2H, δ(7.54).

Example 22

In a 100 ml reactor, 68.0 g of furan, 78.5 g of maleic anhydride, and 100 ml of toluene were added, and reacted at 50° C. for 8 hours. The resultant was cooled, crystallized, and dried to give white crystals of 2,3-dicarboxylic anhydride-7-oxabicyclo[2.2.1]hept-5-ene monomer, with a yield of 92%. It was showed from the $^1$H-NMR (400 MHz, CDCl$_3$) spectrum that there were three peaks of CH, 2H of the ring, δ(3.18, 5.46, 6.58), respectively.

Figure 3:
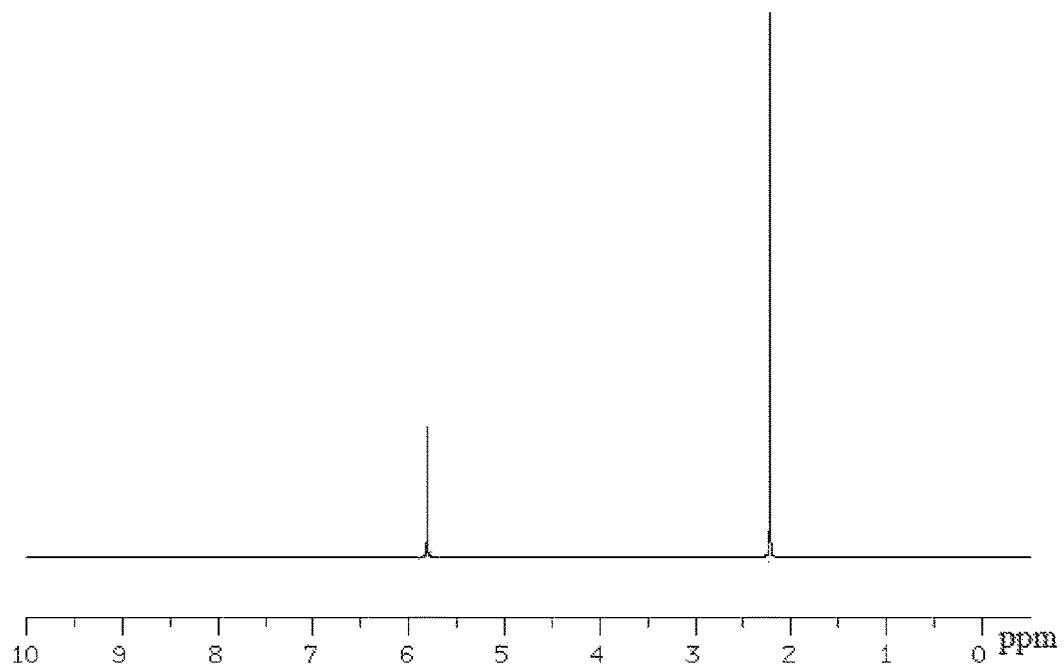
FIG. 3 shows an $^1$H-NMR spectrum of 2,5-dimethylfuran obtained in Example 22.

16.6 g of 2,3-dicarboxylic anhydride-7-oxabicyclo[2.2.1]hept-5-ene monomer was added into a 250 ml reactor. 28.4 g of iodomethane and 0.02 mol of concentrated sulfuric acid were added thereto and reacted at 40° C. for 20 hours. After the reaction was finished, the temperature was reduced to room temperature. The resultant was distilled under reduced pressure to give 2,5-dimethylfuran having a boiling point ranging from 92° C. to 94° C., and the yield was 87%. It was showed from the $^1$H-NMR (400 MHz, CDCl$_3$) spectrum that in the furan ring, CH, 2H, δ(5.81); CH$_3$, 6H, δ(2.23), as shown in FIG. 3.

Example 23

In a 500 ml reactor, 68.0 g of furan, 19.6 g of maleic anhydride, and 20 ml of dichloromethane were added, and reacted at 100° C. for 0.5 hour. The resultant was cooled, crystallized, and dried to give white crystals of 2,3-dicarboxylic anhydride-7-oxabicyclo[2.2.1]hept-5-ene monomer, with a yield of 90%. It was showed from the $^1$H-NMR (400 MHz, CDCl$_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene monomer was added into a 250 ml reactor. 14.2 g of iodomethane and 0.005 mol of concentrated hydrochloric acid were added thereto and reacted at 20° C. for 24 hours. After the reaction was finished, the temperature was increased to room temperature. The resultant was distilled under reduced pressure to give 2,5-dimethylfuran having a boiling point ranging from 92° C. to 94° C., and the yield was 85%. It was showed from the $^1$H-NMR (400 MHz, CDCl$_3$) spectrum that: furan ring: CH, 2H, δ(5.81); CH$_3$, 6H, δ(2.23).

Example 24

In a 200 ml reactor, 68.0 g of furan, 196 g of maleic anhydride, and 800 ml of trichloromethane were added, and reacted at 80° C. for 1 hour. The resultant was cooled, crystallized, and dried to give white crystals of 2,3-dicarboxylic anhydride-7-oxabicyclo[2.2.1]hept-5-ene monomer, with a yield of 96%. It was showed from the $^1$H-NMR (400 MHz, CDCl$_3$) spectrum that there were three peaks of CH, 2H of the ring, δ(3.18, 5.46, 6.58), respectively.

8.3 g of 2,3-dicarboxylic anhydride-7-oxabicyclo[2.2.1]hept-5-ene monomer was added into a 100 ml reactor. 78.0 g of iodoethane and 0.005 mol of concentrated nitric acid were added thereto and reacted at 60° C. for 16 hours. After the reaction was finished, the temperature was reduced to room temperature. The resultant was distilled under reduced pressure to give 2,5-diethylfuran, with a yield of 92%. It was showed from the $^1$H-NMR (400 MHz, CDCl$_3$) spectrum that: furan ring: CH, 2H, δ(5.76); CH$_2$, 4H, δ(2.44); CH$_3$, 6H, δ(1.24).

Example 25

In a 500 ml reactor, 68.0 g of furan, 147 g of maleic anhydride, and 400 ml of petroleum ether were added, and reacted at 65° C. for 4 hours. The resultant was cooled, crystallized, and dried to give white crystals of 2,3-dicarboxylic anhydride-7-oxabicyclo[2.2.1]hept-5-ene monomer, with a yield of 92%. It was showed from the $^1$H-NMR (400 MHz, CDCl$_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene monomer was added into a 100 ml reactor. n-chloropropane and 0.0004 mol of concentrated phosphoric acid were added thereto and reacted at 100° C. for 10 hours. After the reaction was finished, the temperature was reduced to room temperature. The resultant was distilled under reduced pressure to give 2,5-di-n-propylfuran, with a yield of 87%. It was showed from the $^1$H-NMR (400 MHz, CDCl$_3$) spectrum that: furan ring: CH, 2H, δ(5.76); CH$_2$, 4H, δ(2.44); CH$_2$, 4H, δ(1.52); CH$_3$, 6H, δ(0.96).

Example 26

In a 500 ml reactor, 68.0 g of furan, 117.7 g of maleic anhydride, and 200 ml of acetone were added, and reacted at 30° C. for 12 hours. The resultant was cooled, crystallized, and dried to give white crystals of 2,3-dicarboxylic anhydride-7-oxabicyclo[2.2.1]hept-5-ene monomer, with a yield of 88%. It was showed from the $^1$H-NMR (400 MHz, CDCl$_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene monomer was added into a 100 ml reactor. 47.1 g of 2-chloropropane and 0.012 mol of methanesulfonic acid were added thereto and reacted at 120° C. for 4 hours. After the reaction was finished, the temperature was reduced to room temperature. The resultant was distilled under reduced pressure to give 2,5-di-isopropylfuran, with a yield of 89%. It was showed from the $^1$H-NMR (400 MHz, CDCl$_3$) spectrum that: furan ring: CH, 2H, δ(5.76); CH, 2H, δ(3.30); CH$_3$, 6H, δ(1.33).

Example 27

In a 1000 ml reactor, 68.0 g of furan, and 39.2 g of maleic anhydride were added, and reacted at 10° C. for 24 hours. The resultant was crystallized, and dried to give white crystals of 2,3-dicarboxylic anhydride-7-oxabicyclo[2.2.1]hept-5-ene monomer, with a yield of 90%. It was showed from the $^1$H-NMR (400 MHz, CDCl$_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene monomer was added into a 100 ml reactor. 360.8 g of n-iodobutane and 0.06 mol of benzene methyl sulfonic acid were added thereto and reacted at 160° C. for 1 hour. After the reaction was finished, the temperature was reduced to room temperature. The resultant was distilled under reduced pressure to give 2,5-di-n-propylfuran, with a yield of 88%. It was showed from the $^1$H-NMR (400 MHz, CDCl$_3$) spectrum that: furan ring: CH, 2H, δ(5.76); CH$_2$, 4H, δ(2.42); CH$_2$, 4H, δ(1.66); CH$_2$, 4H, δ(1.33); CH$_3$, 6H, δ(0.96).

Example 28

In a 500 ml reactor, 68.0 g of furan, 14.7 g of maleic anhydride, and 60 ml of ethanol were added, and reacted at −5° C. for 48 hours. The resultant was crystallized and dried to give white crystals of 2,3-dicarboxylic anhydride-7-oxabicyclo[2.2.1]hept-5-ene monomer, with a yield of 90%. It was showed from the $^1$H-NMR (400 MHz, CDCl$_3$) spectrum that there were three peaks of CH, 2H of the ring, δ(3.18, 5.46, 6.58), respectively.

16.6 g of 2,3-dicarboxylic anhydride-7-oxabicyclo[2.2.1]hept-5-ene monomer was added into a 250 ml reactor. 198.8 g of iodomethane and 0.084 mol of AlCl$_3$ were added thereto and reacted at 120° C. for 2 hours. After the reaction was finished, the temperature was reduced to room temperature. The resultant was distilled under reduced pressure to give 2,5-dimethylfuran having a boiling point ranging from 92° C. to 94° C. and the yield was 93%. It was showed from the $^1$H-NMR (400 MHz, CDCl$_3$) spectrum that: furan ring: CH, 2H, δ(5.81); CH$_3$, 6H, δ(2.23).

Example 29

In a 200 ml reactor, 68.0 g of furan, 58.8 g of maleic anhydride, and 200 ml of trichloromethane were added, and reacted at 25° C. for 10 hours. The resultant was cooled, crystallized, and dried to give white crystals of 2,3-dicarboxylic anhydride-7-oxabicyclo[2.2.1]hept-5-ene monomer, with a yield of 90%. It was showed from the $^1$H-NMR (400 MHz, CDCl$_3$) spectrum that there were three peaks of CH, 2H of the ring, δ(3.18, 5.46, 6.58), respectively.

8.3 g of 2,3-dicarboxylic anhydride-7-oxabicyclo[2.2.1]hept-5-ene monomer was added into a 100 ml reactor. 78.0 g of iodoethane and 0.025 mol of boron trifluoride ethyl ether complex were added thereto and reacted at 80° C. for 6 hours. After the reaction was finished, the temperature was reduced to room temperature. The resultant was distilled under reduced pressure to give 2,5-diethylfuran, with a yield of 91%. It was showed from the $^1$H-NMR (400 MHz, CDCl$_3$) spectrum that: furan ring: CH, 2H, δ(5.76); CH$_2$, 4H, δ(2.44); CH$_3$, 6H, δ(1.24).

Example 30

6.8 g of furan was added into a 100 ml reactor, then 20.4 g of acetic anhydride and 0.01 mol of concentrated sulfuric acid were added thereto and reacted at 140° C. for 8 hours. After the reaction was finished, the temperature was reduced to room temperature. The resultant was distilled to remove acetic anhydride under reduced pressure and sublimated to give white crystals of 2,5-diacetylfuran having a melting point ranging from 135° C. to 136° C., and the yield was 64%. The molecular weight of 2,5-diacetylfuran was 152.1, which was measured by liquid chromatography-mass spectrometry (LC-MS). It was showed from the $^1$H-NMR (400 MHz, CDCl$_3$) spectrum that: furan ring: CH, 2H, δ(7.24); CH$_3$, 6H, δ(2.59). Elemental analysis for C$_8$H$_8$O$_3$: Calculated: C: 63.15, H: 5.30, O: 31.55. Found: C: 62.70, H: 5.29, O: 31.67.

Example 31

6.8 g of furan was added into a 100 ml reactor, then 15.7 g of acetyl chloride and 0.005 mol of SnCl$_4$ were added thereto and reacted at 60° C. for 12 hours. After the reaction was finished, the temperature was reduced to room temperature. The resultant was distilled to remove acetyl chloride under reduced pressure and sublimated to give white crystals of 2,5-diacetylfuran having a melting point ranging from 135° C. to 136° C., and the yield was 62%. The molecular weight of 2,5-diacetylfuran was 152.1, which was measured by liquid chromatography-mass spectrometry (LC-MS). It was showed from the $^1$H-NMR (400 MHz, CDCl$_3$) spectrum that: furan ring: CH, 2H, δ(7.24); CH$_3$, 6H, δ(2.59). Elemental analysis for C$_8$H$_8$O$_3$: Calculated: C: 63.15, H: 5.30, O: 31.55. Found: C: 62.80, H: 5.37, O: 31.32.

Example 32

6.8 g of furan was added into a 200 ml reactor, then 73.1 g of propionic anhydride and 0.010 mol of concentrated hydrochloric acid were added thereto and reacted at 40° C. for 16 hours. After the reaction was finished, the temperature was reduced to room temperature. The resultant was distilled to remove propionic anhydride under reduced pressure and sublimated to give white crystals of 2,5-dipropionylfuran, with a yield of 67%. The molecular weight of 2,5-dipropionylfuran was 180.1, which was measured by liquid chromatography-mass spectrometry (LC-MS). It was showed from the $^1$H-NMR (400 MHz, CDCl$_3$) spectrum that: furan ring: CH, 2H, δ(7.24); CH$_2$, 4H, δ(2.78); CH$_3$, 6H, δ(1.22). Elemental analysis for C$_{10}$H$_{12}$O$_3$: Calculated: C: 66.65, H: 6.71, O: 26.64. Found: C: 66.7, H: 6.60, O: 27.03.

Example 33

6.8 g of furan was added into a 250 ml reactor, then 102.6 g of chloroacetic anhydride and 0.030 mol of concentrated nitric acid were added thereto and reacted at 100° C. for 5 hours. After the reaction was finished, the temperature was reduced to room temperature. The resultant was distilled to remove chloroacetic anhydride under reduced pressure and sublimated to give white crystals of 2,5-dichloroacetylfuran, with a yield of 62%. The molecular weight of 2,5-dichloroacetylfuran was 221.0, which was measured by liquid chromatography-mass spectrometry (LC-MS). It was showed from the $^1$H-NMR (400 MHz, CDCl$_3$) spectrum that: furan ring: CH, 2H, δ(7.24); CH$_2$Cl, 4H, δ(4.83).

Example 34

6.8 g of furan was added into a 250 ml reactor, then 57.8 g of trifluoroacetic anhydride and 0.005 mol of concentrated hydrochloric acid were added thereto and reacted at 80° C. for 2 hours. After the reaction was finished, the temperature was reduced to room temperature. The resultant was distilled to remove trifluoroacetic anhydride under reduced pressure and sublimated to give white crystals of 2,5-di(trifluoroacetyl)furan, with a yield of 66%. The molecular weight of 2,5-di(trifluoroacetyl)furan was 260.1, which was measured by liquid chromatography-mass spectrometry (LC-MS). It was showed from the $^1$H-NMR (400 MHz, CDCl$_3$) spectrum that: furan ring: CH, 2H, δ(8.14).

Example 35

6.8 g of furan was added into a 100 ml reactor, then 15.5 g of heptafluorobutyric anhydride and 0.005 mol of concentrated phosphoric acid were added thereto and reacted at 140° C. for 2 hours. After the reaction was finished, the temperature was reduced to room temperature. The resultant was distilled to remove heptafluorobutyric anhydride under reduced pressure and sublimated to give crystals of 2,5-di(heptafluorobutyryl)furan, with a yield of 67%. The molecular weight of 2,5-di-heptafluorobutyrylfuran was 360.1, which was measured by liquid chromatography-mass spectrometry (LC-MS). It was showed from the $^1$H-NMR (400 MHz, CDCl$_3$) spectrum that: furan ring: CH, 2H, δ(7.34).

Example 36

6.8 g of furan was added into a 250 ml reactor, then 28.4 g of iodomethane and 0.01 mol of concentrated sulfuric acid were added thereto and reacted at 80° C. for 10 hours. After the reaction was finished, the temperature was reduced to room temperature. The resultant was distilled under reduced pressure to give 2,5-dimethylfuran having a boiling point ranging from 92° C. to 94° C., and the yield was 64%. It was showed from the $^1$H-NMR (400 MHz, CDCl$_3$) spectrum that in the furan ring, CH, 2H, δ(5.81); CH$_3$, 6H, δ(2.23).

Example 37

6.8 g of furan was added into a 250 ml reactor, then 14.2 g of iodomethane and 0.008 mol of concentrated hydrochloric acid were added thereto and reacted at 20° C. for 24 hours. After the reaction was finished, the temperature was increased to room temperature. The resultant was distilled under reduced pressure to give 2,5-dimethylfuran having a boiling point ranging from 92° C. to 94° C., and the yield was 61%. It was showed from the $^1$H-NMR (400 MHz, CDCl$_3$) spectrum that: furan ring: CH, 2H, δ(5.81); CH$_3$, 6H, δ(2.23).

Example 38

6.8 g of furan was added into a 250 ml reactor, then 78.0 g of iodoethane and 0.010 mol of concentrated nitric acid were added thereto and reacted at 60° C. for 16 hours. After the reaction was finished, the temperature was reduced to room temperature. The resultant was distilled under reduced pressure to give 2,5-diethylfuran, with a yield of 71%. It was showed from the $^1$H-NMR (400 MHz, CDCl$_3$) spectrum that: furan ring: CH, 2H, δ(5.76); CH$_2$, 4H, δ(2.44); CH$_3$, 6H, δ(1.24).

While the present application has been described above with respect to the preferred Examples, these Examples are not intended to limit the claims. Various possible modifications or changes may be made by those skilled in the art without departing from the spirit and purview of the present application. Therefore, the protection scope shall be determined by the appended claims.

The invention claimed is:

1. A method for preparing a 2,5-disubstituted furan compound, wherein the 2,5-disubstituted furan compound is prepared by reacting 2,3-dicarboxylic anhydride-7-oxabicyclo[2.2.1]hept-5-ene with an acylating reagent which is an anhydride.

2. The method according to claim 1, wherein the anhydride is at least one selected from the compounds with the chemical structure formula represented by Formula I:

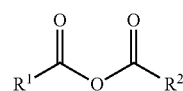

Formula I wherein, R$^1$ is hydrogen or an alkyl group with carbon atoms from 1 to 20; or R$^1$ is a group which is selected from groups with carbon atoms from 1 to 20 and comprising at least one group selected from halogen, aryl, heteroaryl, carbonyl, aliphatic group, nitrile group;

R$^2$ is hydrogen or an alkyl group with carbon atoms from 1 to 20; or R$^2$ is a group which is selected from groups with carbon atoms from 1 to 20 carbon atoms and comprising at least one group selected from halogen, aryl, heteroaryl, carbonyl, aliphatic group, nitrile group.

3. The method according to claim 1, wherein the 2,5-disubstituted furan compound is at least one selected from the compounds with the chemical structure formula represented by Formula IV or Formula V:

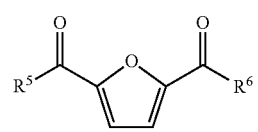

Formula IV wherein, $R^5$ is hydrogen or an alkyl group with carbon atoms from 1 to 20; or $R^5$ is selected from groups with carbon atoms from 1 to 20 and comprising at least one group selected from the list consisting of halogen, aryl, heteroaryl, carbonyl, aliphatic group, nitrile group;

$R^6$ is hydrogen or an alkyl group with carbon atoms from 1 to 20; or $R^6$ is selected from groups with carbon atoms from 1 to 20 and comprising at least one group selected from the list consisting of halogen, aryl, heteroaryl, carbonyl, aliphatic group, nitrile group;

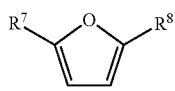

Formula V wherein, $R^7$ is an alkyl group with carbon atoms from 1 to 20; and $R^8$ is an alkyl group with carbon atoms from 1 to 20.

4. The method according to claim 1, wherein the 2,5-disubstituted furan compound is at least one selected from 2,5-diacetylfuran, 2,5-dihaloacetylfuran, 2,5-dimethylfuran, 2,5-diethylfuran.

5. The method according to claim 1, wherein the reaction of 2,3-dicarboxylic anhydride-7-oxabicyclo[2.2.1]hept-5-ene with the acylating reagent is performed at a temperature ranging from 10° C. to 200° C. and for a time ranging 0.1 to 48 hours.

6. The method according to claim 1, wherein, in the reaction of 2,3-dicarboxylic anhydride-7-oxabicyclo[2.2.1]hept-5-ene with the acylating reagent, the molar ratio of the acylating reagent to 2,3-dicarboxylic anhydride-7-oxabicyclo[2.2.1]hept-5-ene and/or furan is that:

moles of the acylating reagent:(moles of 2,3-dicarboxylic anhydride-7-oxabicyclo[2.2.1]hept-5-ene+moles of furan) is in a range from 1:1 to 20:1.

7. The method according to claim 1, wherein an acid catalyst is used in the reaction of 2,3-dicarboxylic anhydride-7-oxabicyclo[2.2.1]hept-5-ene with the acylating reagent; and the molar ratio of the acid catalyst to the acylating reagent is that moles of the acid catalyst:moles of the acylating reagent is in a range from 0.002%:1 to 20%:1.

8. The method according to claim 7, wherein the acid catalyst is at least one selected from sulfuric acid, nitric acid, phosphoric acid, hydrochloric acid, methanesulfonic acid, aluminum chloride, zinc chloride, tin chloride, boron trifluoride ethyl ether complex.

9. The method according to claim 1, wherein the anhydride is at least one selected from formic anhydride, acetic anhydride, propionic anhydride, butyric anhydride, pentanoic anhydride, caproic anhydride, heptanoic anhydride, octanoic anhydride, nonanoic anhydride, capric anhydride, undecanoic anhydride, dodecanoic anhydride, tridecanoic anhydride, tetradecanoic anhydride, pentadecanoic anhydride, hexadecanoic anhydride, heptadecanoic anhydride, octadecanoic anhydride, chloroacetic anhydride, benzoic anhydride, trifluoroacetic anhydride, trichloroacetic anhydride, tribromoacetic anhydride, triiodoacetic anhydride, heptafluorobutyric anhydride, pentafluoropropionic anhydride.

10. The method according to claim 2, wherein $R^1$ and $R^2$ in Formula I are each independently selected from H, —$CH_3$, —$CH_2CH_3$, —$CHCH_3CH_3$, —$CF_3$, —$CCl_3$, —$CBr_3$, —$CI_3$, —$CH_2F$, —$CH_2Cl$, —$CH_2Br$, —$CH_2I$, —$CHCl_2$, —$CH_2CH_2F$, —$CH_2CH_2Cl$, —$CH_2CH_2Br$, —$CH_2CH_2I$, —$CH_3CHBr$, —$CF_3CF_2$, —$CF_3CF_2CF_2$, furyl, —COCl, $CH_3CH_2OCO$—, $C_6H_5CH_2$—, —$C_6H_5$, $CH_3OCO$—, $C_6H_5CH_2CH_2$—, $(C_6H_5)_2CH$—.

11. The method according to claim 3, wherein $R^5$ and $R^6$ in Formula IV are each independently selected from H, —$CH_3$, —$CH_2CH_3$, —$CHCH_3CH_3$, —$CF_3$, —$CCl_3$, —$CBr_3$, —$CI_3$, —$CH_2F$, —$CH_2Cl$, —$CH_2Br$, —$CH_2I$, —$CHCl_2$, —$CH_2CH_2F$, —$CH_2CH_2Cl$, —$CH_2CH_2Br$, —$CH_2CH_2I$, —$CH_3CHBr$, —$CF_3CF_2$, —$CF_3CF_2CF_2$, furyl, —COCl, $CH_3CH_2OCO$—, $C_6H_5CH_2$—, —$C_6H_5$, $CH_3OCO$—, $C_6H_5CH_2CH_2$—, $(C_6H_5)_2CH$—.

12. The method according to claim 3, wherein $R^7$ and $R^8$ in Formula V are each independently selected from methyl, ethyl, propyl, butyl, isopropyl, isobutyl, tert-butyl, cyclohexyl.

13. The method according to claim 2, wherein $R^1$ and $R^2$ in Formula I are the same group.

14. The method according to claim 3, wherein $R^7$ and $R^8$ in Formula V are the same group.

* * * * *